United States Patent [19]
Parnoff et al.

[11] Patent Number: 5,146,283
[45] Date of Patent: Sep. 8, 1992

[54] SPECTROPHOTOMETER SAMPLE CELL

[75] Inventors: George K. Parnoff, Walnut Creek; Emery Major, Pt. Richmond, both of Calif.

[73] Assignee: Andros Incorporated, Berkeley, Calif.

[21] Appl. No.: 675,151

[22] Filed: Mar. 26, 1991

[51] Int. Cl.[5] .......................................... G01N 21/05
[52] U.S. Cl. ................................... 356/246; 356/440; 250/576
[58] Field of Search ................ 356/51, 244, 246, 410, 356/411, 440; 250/339, 343, 373, 576

[56] References Cited

U.S. PATENT DOCUMENTS

| | | | |
|---|---|---|---|
| 3,480,784 | 11/1969 | Pierce | 356/246 |
| 3,614,243 | 10/1971 | Harvey | 356/246 |
| 3,700,338 | 10/1972 | Trundle | 356/246 |
| 3,887,473 | 6/1975 | Sternberg et al. | 250/345 |
| 4,067,653 | 1/1978 | Fletcher et al. | 356/246 |
| 4,177,381 | 12/1979 | McClatchie et al. | 250/343 |
| 4,468,124 | 8/1984 | Berick | 356/411 |
| 4,501,968 | 2/1985 | Ebi et al. | 250/343 |
| 4,736,103 | 4/1988 | Nelson et al. | 250/343 |

FOREIGN PATENT DOCUMENTS 15439 1/1987 Japan ..................... 356/246

OTHER PUBLICATIONS

Swope, *The Review of Scientific Instruments*, vol. 42, No. 10, Oct. 1971, pp. 1502-1504.

*Primary Examiner*—F. L. Evans
*Attorney, Agent, or Firm*—McCubbrey, Bartles, Meyer & Ward

[57] ABSTRACT

A spectrophotometer sample cell is described having a housing defining a frusto-conical chamber with inlet and outlet windows at each end. The inlet window is positioned toward the energy source of the spectrophotometer and the outlet window, which is the larger diameter window, is positioned toward the detector assembly of the spectrophotometer. A single outlet passage is positioned between a pair of inlet passages, the latter being toward respective ends of the chamber. The interior surface of the sample cell is provided with means for preventing a substantial portion of reflected energy impinging on the sample cell walls from reaching the detector. Such means include irregularities, annular walls, and wavelength absorbing colors. A trough is provided in the bottom of the larger end of the frusto-conical chamber for conveying condensate to the outlet passage.

3 Claims, 2 Drawing Sheets

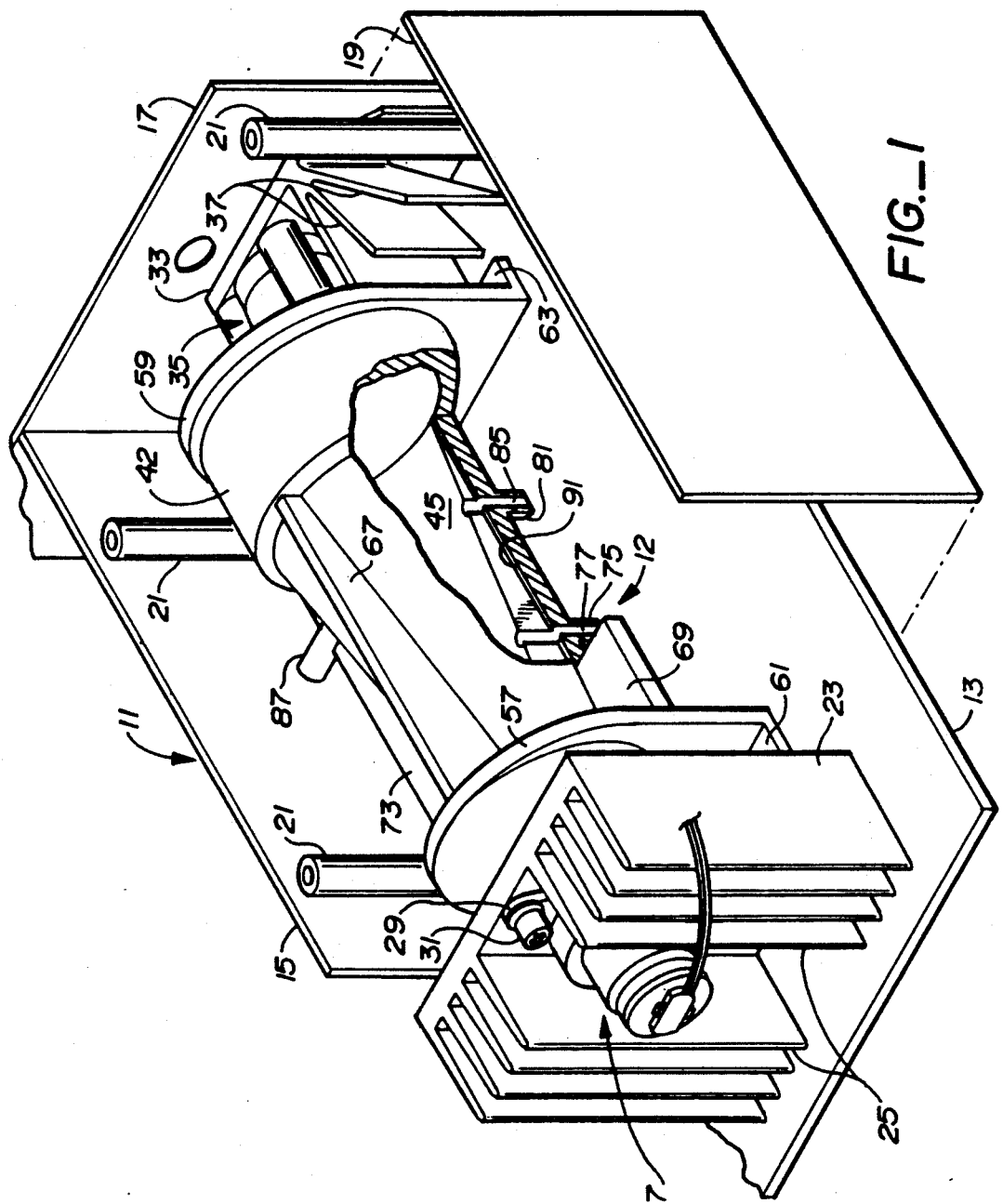
FIG._1

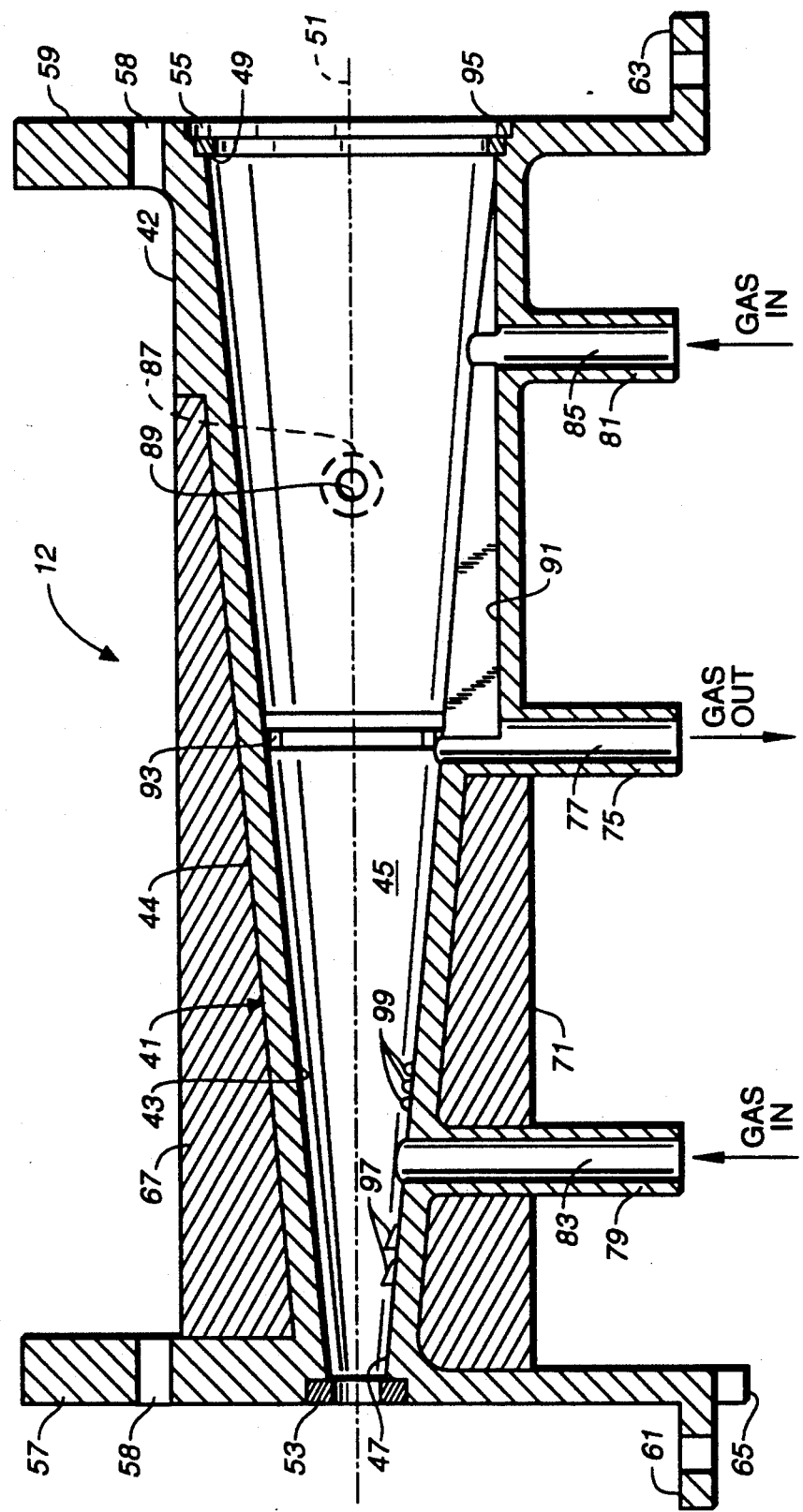
FIG._2

SPECTROPHOTOMETER SAMPLE CELL

This invention relates generally to spectrophotometers. More particularly, the invention relates to an improved sample cell for use in a spectrophotometer for containing a selected volume and path length of gaseous mixture for analysis on a continuing basis.

BACKGROUND OF THE INVENTION

Spectrophotometer typically operates by passing a beam of energy from a source through a gaseous mixture to a detector. The energy beam, which may be infrared, visible light, or any other suitable wavelength, is chosen in accordance with the absorption wavelength or wavelengths of a gas or gases of interest in the gaseous mixture. By detecting or measuring the absorption at each selected wavelength, the presence or concentration of the gas of interest in the gaseous mixture may be determined.

In certain types of spectrophotometer, a sample cell is used for containing a selected volume and path length of the gaseous mixture to be analyzed. Where the gas is to be analyzed on a continuing basis, for example automotive exhaust gas, the sample cell will contain provision for passing the gas of interest into and out of the cell in a desired flow pattern. One example of a sample cell of this type is shown and described in U.S. Pat. No. 4,177,381, McClatchie et al., assigned to the assignee of the present invention.

It has been found advantageous, for certain applications, to reduce the size of the sample cell. By doing so, the volume of gas analyzed is reduced and certain advantages accrue, including a reduction in the pumping capacity required for the gas. One way of reducing the sample cell size is to make the interior of the sample cell frusto-conical in shape. An example of such a cell is shown in U.S. Pat. No. 3,887,473, Sternberg et al.

When a so called conical sample cell is employed in a spectrophotometer, certain problems may be encountered. For example, energy radiated from the source and reflected off of the interior walls of the sample cell may reach the detector. Such reflections have a different path length than radiation reaching the detector directly from the source. Accordingly, aberrations in the reading of the spectrophotometer may be introduced. Another problem may be as a consequence of condensate building up within the sample cell and collecting at the large diameter end of the cell. Without removal, this condensate could result in a erroneous spectrophotometer reading.

SUMMARY OF THE INVENTION

It is an object of the present invention to provide an improved sample cell for use in a spectrophotometer.

Another object of the invention is to provide an improved spectrophotometer sample cell for containing a selected volume and path length of gaseous mixture for analysis on a continuing basis.

A still further object of the invention is to provide a spectrophotometer sample cell which is conical and wherein reflected energy from the spectrophotometer source does not reach the detector.

A still further object of the invention is to provide a conical sample cell for a spectrophotometer wherein condensate does not interfere with the spectrophotometer reading.

These and other objects of the invention will become apparent to those skilled in the art from the following description.

Very generally, the sample cell of the invention is for use in a spectrophotometer wherein a beam of energy from a source is passed through a gaseous mixture to a detector for detecting the absorption of energy by the gaseous mixture in a selected wavelength band. A sample cell contains a selected volume and path length of gaseous mixture for analysis on a continuing basis. The sample cell comprises a housing having an interior surface which defines a frusto-conical chamber of preselected volume. An inlet window is provided at the smaller diameter end of the chamber and an outlet window is provided at the larger diameter end. The inlet window is positioned toward the energy source and the outlet window is positioned toward the detector. The windows define a path length for the beam of energy substantially aligned with the axis of the frusto-conical chamber. An outlet passage for the gaseous mixture communicates with the chamber through the interior surface of the housing. A pair of inlet passages communicate with the chamber through the interior surface of the housing and are positioned on opposite sides of the outlet passage spaced therefrom toward respective ends of the chamber. The interior surface of the sample cell is provided with means which prevent a substantial amount of energy in the beam, reflected off of the interior surface, from reaching the detector. In one embodiment of the invention, the interior surface further defines a trough at the bottom of the larger end of the chamber for conveying condensate to the outlet passage.

DESCRIPTION OF THE DRAWINGS

FIG. 1 is a perspective view, partially exploded, of a portion of a spectrophotometer utilizing a sample cell constructed in accordance with the invention.

FIG. 2 is a sectional view of the sample cell shown in FIG. 1 taken on a plane extending vertically through the axis of the sample cell. Although the vertical fins are integral with the sample cell housing, they are sectioned oppositely in FIG. 2 for clarity.

DETAILED DESCRIPTION OF THE PREFERRED EMBODIMENT

Referring now to FIG. 1, a portion of a spectrophotometer 11 is shown in perspective view. The spectrophotometer 11 comprises a base plate 13, a plurality of side walls 15, 17, and 19, and a top, not shown. A plurality of mounting posts 21 are provided on the side walls for securing the unillustrated top in position.

A mounting casting 23 is supported on the base plate 13 and is provided with a plurality of cooling fins 25. The casting 23 acts as a heat sink for a source assembly 27, which is mounted thereon by suitable means such as mounting flange 29 and screw 31. The source assembly 27 may be of any suitable construction and contains a source for emitting a beam of energy directed into the sample cell. Source assemblies for this purpose are well known in the art. For example, an infrared radiation source assembly typically will include a heater and one or more filters, each of which is designed to pass infrared energy in a preselected wavelength. The source assembly may, for example, contain a rotating filter wheel designed to successively interpose filters into the path of infrared energy. Other types of source assemblies may include a single filter followed by a chopper wheel for periodically interrupting the energy at a preselected frequency. As an alternative, the source assembly may contain a source which emits light in the visible spectrum or in another suitable spectrum, all dependent upon the nature of the gaseous mixture being analyzed.

A detector mounting casting 33 is suitably supported on the base 13 against the wall 17. The casting 33 acts as a heat sink and mounting support for a detector assembly 35. Cooling fins 37 are provided on the casting 33.

The detector assembly 35 may be of any suitable construction, depending upon the gas or gasses of interest. The detector assembly 35 contains suitable filters and a detector designed to detect and emit a signal dependant upon the amplitude of energy passing through the sample cell. Detector assemblies of various types are well known to those skilled in the art.

The sample cell 12 is mounted in a spectrophotometer to the base plate 13 and extends between the source assembly 27 and the detector assembly 35. The sample cell contains a selected volume and path length of the gaseous mixture of interest for analysis on a continuing basis. The construction of the sample cell may be discerned from the following description by reference to both FIGS. 1 and 2.

The sample cell 12 includes a housing 41 which has an interior surface 43 defining a frusto-conical chamber 45. The volume of the chamber is preselected in accordance with the desired overall design parameters of the spectrophotometer. An inlet window 47 and an outlet window 49 are provided at opposite ends of the frusto-conical chamber 45, the outlet window being at the larger end of the chamber and the inlet window being at the smaller diameter end. The inlet window 47 is positioned toward the source assembly 27 and the outlet window 49 is positioned toward the detector assembly 35. Together, the windows 47 and 49 define a path length for the beam of energy emitted by the source assembly substantially aligned with the axis 51 of the frusto-conical chamber 45. A recess 53 is provided in the housing 41 surrounding the window 47 for incorporating an energy transparent plate, not shown. A similar recess 55 is provided in the housing 41 adjacent the window 49 for accommodating a similar energy transparent plate.

The outer surface of the housing 41 has a cylindrical portion 42 toward the large diameter end of the chamber 45, and has a tapered portion 44 which extends from the cylindrical portion 42 toward the small diamter end of the chamber 45.

The opposite ends of the housing 41 are provided with mounting plates 57 and 59, respectively. The mounting plate 57 is provided with a 90° mounting bracket 61 at its lower most end. Similarly, the mounting plate 59 is provided with a pair of 90° mounting feet 63 at the lower most end thereof. Projections 65 extend downwardly from the lower edge of the mounting plate 57 for locating the sample cell 12 on the face plate 13 in suitable openings, not shown, in the base plate. Mounting holes 58 are provided in the plates 57 and 59 at suitable locations.

To enhance structural stability of the sample cell 12, four fins 67, 69, 71, and 73, are provided extending longitudinally of the housing 41 at 90° radial intervals. The fins 67 and 71 are shown in FIG. 2 oppositely cross-hatched from the remainder of the sample cell 12. However, it is to be understood that the fins may be molded integrally with the remaining parts of the sample cell.

The housing 41 is provided with a tubular projection 75 which defines an outlet passage 77 communicating with the chamber 45 through the interior surface 43 of the housing 41. This passage is adapted for connection to conduits, not shown, suitable for evacuating the gaseous mixture from the chamber 45 through the passage 77.

The housing 41 also includes a pair of further tubular projections 79 and 81 extending downwardly from the housing. The tubular projections 79 and 81 define inlet passages 83 and 85, respectively, which communicate with the chamber 45 through the interior surface 43 of the housing 41. The inlet passages 83 and 85 are positioned on opposite sides of the outlet passage 77 and are spaced therefrom toward respective ends of the chamber 45. In the illustrated embodiment, the passage 77 is approximately midway between the ends of the chamber 45, whereas the passages 83 and 85 are positioned slightly closer to the ends of the chamber 45 than to the passage 77. The extensions or projections 79 and 81 are adapted for connection to a source of gas to be analyzed, for example, a supply pump for supplying gas to be analyzed. Gas flows into the chamber 45 from the respective passages 79 and 81, moves toward the center of the chamber 45, and is withdrawn through the passage 77.

A further tubular projection 87 provides a further passage 89 communicating with the chamber 45. The passage 89 is for the purpose of communicating with a pressure detection transducer, not shown, to monitor the pressure of the gas within the chamber 45.

A channel 91 is formed by the housing 41 contiguous with the frusto-conical surface 43. The channel 91 is, in the illustrated embodiment, generally aligned with the fin 71, forming substantially an extension of the fin 71 to the cylindrical outer surface 42. The channel 91 extends from the outlet passage 77 to the larger diameter end of the chamber 45. Any condensate which forms in the chamber 45 toward the larger diameter end from the passage 77 will drain into the channel 91 and from thence through the outlet passage 77. Any condensation forming within the portion of the chamber 45 toward the smaller diameter end from the outlet passage 77 will drain into the outlet passage. Thus, collection of condensate toward the larger diameter end of the frusto-conical chamber 45 is prevented.

In accordance with the invention, the interior surface 43 of the chamber 45 is provided with means for preventing a substantial portion of the energy in the energy beam impinging on the interior surface 43 from reaching the detector. Such means include an annular projection 93 extending inwardly from the chamber interior surface 43 approximately midway between its ends. The annular projection 93 may, for example, be a ring sonically welded to the interior of the housing 41. The portion of the ring 93 opposite the passage 77 is flattened on its lower exterior edge to provide communication from the passage 77 to both sides of the ring or projection 93. A similar annular projection or ring 95 is provided adjacent the window 49, and may also be sonically welded to the housing 41. The rings 93 and 95 serve as apertures for defining the energy beam and for blocking stray rays from reaching the detector.

As a further means for preventing reflected rays from reaching the detector, the interior surface 43 is provided with irregularities such as steps or roughening, shown in part at 97 and 99. It is to be understood that these steps or roughening or any mixture thereof may be extended over all or part of the interior surface 43 as required to prevent reflected rays from reaching the detector.

As a further means of preventing rays impinging on the chamber walls from reaching the detector, the interior surface 43 may be provided with a wavelength absorbing color selected to be at the wavelength of the gas or gases of interest. This prevents stray rays from reaching the detector by absorbing the energy therein.

It may be seen, therefore, that the invention provides an improved sample cell which is of low volume, adapted for gas analysis on a continuing basis, and which prevents reflected rays from the source assembly from reaching the detector assembly. Moreover, inaccuracy as a result of condensation build-up within the sample cell is avoided.

Various modifications of the invention, in addition to those shown and described herein, will become apparent to those skilled in the art from the foregoing description and accompanying drawings. Such modifications are intended to fall within the scope of the appended claims.

What is claimed is:

1. In a spectrophotometer wherein a beam of energy from a source is passed through a gaseous mixture to a detector for detecting the absorption of energy by the gaseous mixture in a selected wavelength band, a sample cell for containing a selected volume and path length of gaseous material for analysis on a continuing basis, said sample cell comprising:

a housing having an interior surface defining a frusto-conical chamber of preselected volume, a pair of windows each disposed at a respective end of said chamber and a trough disposed between said windows in the lowermost portion of said chamber for conveying condensate from said chamber;

said windows being positioned toward said source and said detector to define a path length for the beam of energy substantially aligned with the axis of said frusto-conical chamber;

a pair of inlet passages communicating with said chamber through said interior surface of said housing for introducing the gaseous mixture into said chamber, said inlet passages being disposed on the bottom of and toward respective ends of said chamber; and an outlet passage communicating with said chamber through said interior surface of said housing for removing the gaseous mixture from said chamber, said outlet passage being in communication with said trough and disposed in the lowermost portion of said chamber.

2. A sample cell according to claim 1 wherein said trough extends over a substantial portion of the length of said chamber.

3. A sample cell according to claim 2 wherein said trough is substantially horizontal.

* * * * *